United States Patent
Franke et al.

(10) Patent No.: US 11,993,558 B2
(45) Date of Patent: *May 28, 2024

(54) PROCESS FOR HYDROGENATION OF C9 ALDEHYDES IN AT LEAST TWO HYDROGENATION STAGES

(71) Applicant: Evonik Operations GmbH, Essen (DE)

(72) Inventors: Robert Franke, Marl (DE); Meike Roos, Büdingen (DE); Horst-Werner Zanthoff, Mülheim a.d. Ruhr (DE); Julia Bauer, Haltern am See (DE); Christoph Weber, Wiesbaden (DE); Andrea Heinroth, Möbris (DE); Jan Benedikt Metternich, Recklinghausen (DE)

(73) Assignee: EVONIK OPERATIONS GMBH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/113,755

(22) Filed: Feb. 24, 2023

(65) Prior Publication Data

US 2023/0271904 A1    Aug. 31, 2023

(30) Foreign Application Priority Data

Feb. 25, 2022   (EP) .................................... 22158737

(51) Int. Cl.
| | |
|---|---|
| *C07C 29/141* | (2006.01) |
| *B01J 23/883* | (2006.01) |
| *B01J 23/885* | (2006.01) |
| *B01J 35/56* | (2024.01) |
| *B01J 35/61* | (2024.01) |
| *B01J 35/64* | (2024.01) |

(52) U.S. Cl.
CPC ........... *C07C 29/141* (2013.01); *B01J 23/883* (2013.01); *B01J 23/885* (2013.01); *B01J 35/56* (2024.01); *B01J 35/613* (2024.01); *B01J 35/615* (2024.01); *B01J 35/657* (2024.01)

(58) Field of Classification Search
CPC .............. C07C 29/141; C07C 2523/76; C07C 2523/88; C07C 31/125
See application file for complete search history.

(56) References Cited

U.S. PATENT DOCUMENTS

| | | |
|---|---|---|
| 4,426,541 A | 1/1984 | King et al. |
| 4,960,960 A | 2/1990 | Harrison et al. |
| 11,401,224 B2 | 8/2022 | Roos et al. |
| 2006/0129004 A1 | 6/2006 | Lueken et al. |
| 2009/0018366 A1 | 1/2009 | Berweiler et al. |
| 2012/0253083 A1 | 10/2012 | Kaizik et al. |
| 2013/0109890 A1 | 5/2013 | Van Vliet et al. |
| 2016/0176792 A1 | 6/2016 | Klasovsky et al. |
| 2019/0232257 A1* | 8/2019 | Wieland ................ B01J 8/0278 |
| 2020/0109101 A1 | 4/2020 | Hasselberg et al. |

FOREIGN PATENT DOCUMENTS

| | | |
|---|---|---|
| DE | 102004059292 A1 | 6/2006 |
| EP | 2764916 A1 | 8/2014 |
| EP | 3037400 A1 | 6/2016 |
| EP | 3632885 A1 | 4/2020 |
| WO | 8707598 A1 | 12/1987 |
| WO | 8805767 A1 | 8/1988 |
| WO | 2007028411 A1 | 3/2007 |
| WO | 2011045102 A1 | 4/2011 |
| WO | 2011115695 A1 | 9/2011 |

OTHER PUBLICATIONS

U.S. Appl. No. 18/113,749, filed Feb. 24, 2023 (unpublished).
U.S. Appl. No. 18/113,319, filed Feb. 23, 2023 (unpublished).
European Search Report for EP22158737 dated Aug. 29, 2022.

* cited by examiner

*Primary Examiner* — Jafar F Parsa
(74) *Attorney, Agent, or Firm* — Millen, White, Zelano & Branigan, P.C.; Ryan R. Pool

(57) ABSTRACT

The present invention relates to a process for producing alcohols by hydrogenation of C9 aldehydes. The process according to the invention is performed in two consecutive hydrogenation stages, wherein the first hydrogenation stage employs an activated metal catalyst based on a nickel metal foam and the second stage employs a supported catalyst containing a catalytically active component from the group consisting of nickel, copper, chromium and mixtures thereof.

15 Claims, No Drawings

PROCESS FOR HYDROGENATION OF C9 ALDEHYDES IN AT LEAST TWO HYDROGENATION STAGES

The present invention provides a process for producing alcohols by hydrogenation of C9 aldehydes. The process according to the invention is performed in two consecutive hydrogenation stages, wherein the first hydrogenation stage employs an activated metal catalyst based on a nickel metal foam and the second stage employs a supported catalyst containing a catalytically active component from the group consisting of nickel, copper, chromium and mixtures thereof.

The basic object of petrochemistry is the provision of feedstocks for the chemical industry. This includes the production of aldehydes obtained from olefins by hydroformylation for example. The resulting aldehydes may then be further processed into alcohols by hydrogenation. Industrially, the hydrogenation of aldehydes is typically performed in the gas or liquid phase over heterogeneous catalysts arranged in a fixed bed. Both the catalyst and the process mode in the reaction apparatuses operated therewith are of decisive importance for the process. The catalysts determine for example the intrinsic reaction rate and selectivity of the hydrogenation. In addition, the selection of a suitable catalyst is also important since the aldehydes to be hydrogenated are usually employed as a mixture of structurally isomeric aldehydes and potentially disruptive byproducts which bring about undesired secondary reactions in the hydrogenation and can also damage the hydrogenation catalyst. The process mode of the employed reaction apparatuses makes it possible for example to influence concentrations and mass transfer and heat transfer processes in the reaction system and thus optimally utilize the intrinsic properties of the catalysts.

A person skilled in the art is already aware of a multiplicity of different catalysts for the hydrogenation of aldehydes, for example mixed metal catalysts as in EP 3 037 400 A1 or WO 2011/045102 A1 or activated metal catalysts as in WO 2007/028411 A1. Activated metal catalysts are typically understood as meaning metal alloys applied to metallic, oxidic or carbon-containing supports and activated by leaching, wherein the support may be completely removed.

Depending on the desired influencing of the reaction and the simultaneous mass transfer and heat transfer processes, possible employed reaction apparatuses include a multiplicity of reactor types and combinations of reactor types, as described for example in DE102004059292A1.

There is a continuous need for process improvements in the hydrogenation of aldehydes. The hydrogenation process should feature good activity and alcohol selectivity as well as have the feature that the smallest possible amount of undesired byproducts are formed and/or the largest possible amount of undesired byproducts are decomposed during the process.

This object is achieved by the process according to the invention according to claim 1. Preferred embodiments are specified in the dependent claims. The process according to the invention is a process for producing alcohols by continuous hydrogenation of C9 aldehydes in at least two hydrogenation stages, wherein a stream containing the C9 aldehydes to be hydrogenated is hydrogenated with a hydrogen-containing gas over an activated metal catalyst based on a nickel metal foam in the liquid phase in the first hydrogenation stage comprising at least one recycle reactor, wherein a crude product stream containing at least alcohols and unconverted aldehydes, of which a first portion is recycled and a second portion is passed to the second hydrogenation stage, is withdrawn from the at least one recycle reactor, the second portion of the crude product stream is hydrogenated with a hydrogen-containing gas over a supported catalyst comprising a catalytically active component and a support material in the liquid phase in the second hydrogenation stage comprising at least one reactor operated in straight pass, wherein the catalytically active component is selected from the group consisting of nickel, copper, chromium and mixtures thereof and wherein the support material consists to an extent of more than 90% by weight of an oxidic material selected from the group consisting of aluminum oxide, aluminum silicate, silicon dioxide, titanium dioxide, zirconium oxide and mixtures of two or more thereof.

The process employs a stream which contains the C9 aldehydes to be hydrogenated and is passed to the first hydrogenation stage. Such streams may for example derive from an upstream continuous or discontinuous hydroformylation of C8 olefins. After the hydroformylation at least one separation of the typically employed homogeneous catalyst may be carried out. By contrast, when using heterogenized catalyst systems, as disclosed for example in EP 3 632 885 A1, a separation of the catalyst system is not necessary. Processes for producing the aldehydes according to the invention by hydroformylation are familiar to those skilled in the art and will not be described in detail here. In a preferred embodiment of the present invention the stream which contains the C9 aldehydes to be hydrogenated is an isononanal stream. An isononanal stream in the context of the present invention is a mixture of different isomeric C9 aldehydes. Such mixtures are obtained on a large industrial scale from C8 olefin fractions by hydroformylation, wherein the C8 olefins are obtainable for example by oligomerization of C4 olefins, i.e. butenes. These processes are familiar to those skilled in the art.

The employed aldehyde-containing stream is in the first hydrogenation stage hydrogenated using an activated metal catalyst based on a nickel metal foam. Such catalysts are known for example from EP 2 764 916 A1 where they are referred to as surface-modified metal foam bodies. The production of these catalysts may be effected for example by the following process:

a) A commercially available nickel metal foam is treated with an adhesion promoter (for example polyvinylpyrrolidone or a polyethyleneimine) and subsequently coated with aluminum powder, wherein the application of the aluminum powder is preferably effected by spraying, scattering reporting and wherein the aluminum powder consists to an extent of 90% to 99.8% by weight of aluminum particles and has an oxygen content of 0.01% to 0.85% by weight in each case based on the total weight of the aluminum powder. The aluminum particles present in the aluminum powder preferably have a particle size in the range from 5 µm to 200 µm with a $d_{90}$ in the range from 50 to 75 µm b) In a subsequent heat treatment in the absence of oxygen aluminum is dissolved in the nickel metal foam to form intermetallic phases and simultaneously the adhesion promoter is removed. The structure and pore structure of the nickel metal foam are completely retained. The heat treatment may be performed at a temperature in the range from 500° C. to 1000° C. and is preferably carried out in two or more stages at different temperatures, wherein in a first stage the adhesion promoter is removed ("debindering") and in a subsequent stage at higher temperature the dissolution of the aluminum in the nickel foam to form intermetallic phases is effected. It is particularly preferable when a maximum temperature of 800° C. is not exceeded during the entire heat treatment.

c) Subsequently a comminution and/or separation of the material may be effected provided this has not already taken place in a forming step before the heat treatment. Comminution of the material may be effected using thermal or mechanical cutting processes. Comminution is preferably carried out by laser cutting or laser beam cutting or using suitable cutting blades.

d) The actual catalyst is produced in the last step by leaching out at least a portion of the aluminum present in the alloy. This is done using aqueous basic solutions, preferably alkali metal hydroxide solutions, for example produced by dissolving sodium hydroxide, potassium hydroxide or lithium hydroxide in water. The concentration of the aqueous alkali metal hydroxide solutions used in this process step is generally in a range between 0.1% to 60% by weight. The leaching out of the aluminium is preferably effected with a 5% to 50% by weight, particularly preferably 5% to 25% by weight, aqueous sodium hydroxide solution at a temperature in the range from 20° C. to 100° C., preferably in a range from 40° C. to 85° C., particularly preferably in a range from 50° C. to 70° C. The reaction times of the sodium hydroxide solution with the aluminium-alloyed nickel metal foam may be between 5 and 300 minutes. The reaction time of the sodium hydroxide solution with the aluminum-alloyed nickel foam is preferably in the range from 30 to 180 minutes.

In a preferred embodiment of the present invention the activated metal catalyst based on a nickel metal foam employed in the first hydrogenation stage is free from organic constituents, i.e. the sum of the weight fractions of carbon and carbon-containing compounds is less than 0.2% by weight of the total weight of the catalyst. This property relates to the catalyst directly after production and thus before use in the hydrogenation. During the hydrogenation the activated metal catalyst based on a nickel metal foam may become coated with organic constituents, i.e. exhibit higher proportions of carbon-containing compounds.

The activated metal catalyst based on a nickel metal foam according to the present invention preferably contains 80% to 95% by weight of nickel, 5% to 15% by weight of aluminum and optionally 0% to 5% by weight of promoters, for example copper or molybdenum, in each case based on the total weight of the catalyst. In a preferred embodiment the activated metal catalysts based on a nickel metal foam additionally contains 0.01% to 3% by weight of molybdenum, particularly preferably 0.2% to 1.5% by weight of molybdenum and very particularly preferably 0.3% to 0.7% by weight of molybdenum in each case based on the total weight of the catalyst.

The activated metal catalyst based on a nickel metal foam employed in the first hydrogenation stage is in principle not subject to any structural limitations provided sufficient contact with the aldehydes to be converted is ensured. However, it is preferable when the activated metal catalysts based on a nickel metal foam has a BET surface area of 1 to 200 m²/g, preferably 5 to 100 m²/g, particularly preferably 15 to 80 m²/g. As is well-known the BET surface area may be determined by gas adsorption. The activated metal catalyst based on a nickel metal foam may need to be stored under water on account of its properties.

The hydrogenation process according to the invention employs different catalysts in the two hydrogenation stages. It is advantageous when the volume fraction of the activated metal catalyst based on a nickel metal foam in the total catalyst volume of all hydrogenation stages is from 30% to 80%, preferably 35% to 60%. This makes it possible to achieve particularly efficient reaction management.

The hydrogenation in the first hydrogenation stage is performed in at least one recycle reactor, where a portion of the crude product stream is recycled. In a preferred embodiment of the present invention the first hydrogenation stage consists of a recycle reactor. The activated metal catalyst based on a nickel metal foam is employed in the at least one recycle reactor as a fixed bed or as a structured packing.

The hydrogenation in the first hydrogenation stage may generally be performed at a pressure of 5 to 150 bar, preferably 15 to 50 bar, particularly preferably 20 to 45 bar. A pressure of 20 bar to 30 bar is very particularly preferred. The temperature during hydrogenation in the first hydrogenation stage of the process according to the invention is preferably in the range from 50° C. to 250° C., preferably 80° C. to 200° C., particularly preferably from 100° C. to 190° C.

The hydrogenation in the first hydrogenation stage may further be performed in the presence of a solvent inert under the hydrogenation conditions. Inert solvents are known to those skilled in the art but are preferably selected from the group consisting of hydrocarbons and alcohols, preferably the alcohols obtained from the employed aldehydes. When using at least one recycle reactor the alcohol obtained from the hydrogenation may also function as a solvent. The hydrogenation may also be performed in the presence of an aqueous phase, for example process water from the preceding production of the aldehydes or the hydrogenation itself. However, it is preferable according to the invention when no additional aqueous phase is added to the hydrogenation in the first stage.

The hydrogen-containing gas employed for the hydrogenation in the first hydrogenation stage may be either hydrogen or else a gas mixture which contains not only hydrogen but also one or more gases inert under hydrogenation conditions. It should be ensured that the amount of hydrogen is high enough to allow the hydrogenation to be performed to a sufficient extent. It is further preferable when the hydrogen is employed in a certain stoichiometric excess having regard to the aldehydes to be hydrogenated. The stoichiometric excess of hydrogen relative to the aldehydes to be hydrogenated is preferably in the range of 5% to 90%, particularly preferably between 20% and 70%.

The reported process conditions in the first hydrogenation stage make it possible to achieve high reaction conversions. It is preferable when the conversion in the hydrogenation in the first hydrogenation stage is at least 85%, preferably at least 90%, particularly preferably at least 95%.

A crude product stream containing at least alcohols and unconverted aldehydes is withdrawn from the first hydrogenation stage. At least a portion of the stream is passed to the second hydrogenation stage and therein subjected to a second hydrogenation. Since the first hydrogenation stage comprises a recycle reactor a first portion of the crude product stream is recycled and a second portion of the crude product stream is passed to the second hydrogenation stage.

The second hydrogenation stage of the process according to the invention employs at least one reactor operated in straight pass to convert at least a portion of the as yet unhydrogenated aldehydes. In addition, byproducts from the hydroformylation or the first hydrogenation stage may be converted and thus decomposed in the second stage. For the present invention this includes for example acetal cleavage, by which acetals present as byproduct are removed. This employs a suitable hydrogenation catalyst which is distinct from the catalyst in the first hydrogenation stage and which comprises a catalytically active component and a support material.

According to the invention the catalytically active component is selected from the group consisting of nickel, copper, chromium and mixtures thereof. In a preferred embodiment of the present invention the catalyst is free from chromium, i.e. contains, based on the total composition of at least catalytically active component and support material, less than 50 ppmw of chromium. It is particularly preferable when the catalytically active component is a mixture of copper and nickel. Catalysts containing corresponding mixtures of nickel and copper are disclosed for example in EP 3 037 400 A1 which also describes the production of such a catalyst.

The support material of the supported catalyst employed in the second hydrogenation stage consists to an extent of more than 90% by weight of an oxidic material selected from the group consisting of aluminum oxide, aluminum silicate, silicon dioxide, titanium dioxide, zirconium oxide and mixtures of two or more thereof. The support material for the supported catalyst is preferably aluminum oxide, aluminum silicate or silicon dioxide. In a particularly preferred embodiment the support material is aluminum oxide. The support material employed for the catalyst may have a BET surface area of 70 to 350 $m^2/g$, preferably 150 to 280 $m^2/g$. As is well-known the BET surface area may be determined by gas adsorption.

The supported catalyst employed in the second hydrogenation stage may contain further substances. For example the supported catalysts according to the invention may contain alkali metal or alkaline earth metal compounds, in particular alkali metal or alkaline earth metal oxides. These may be added during production of the catalysts or also occur in traces in the employed support material. Further auxiliaries may additionally be added during production of the supported catalyst. One example thereof is graphite which may be employed as a processing aid.

The process conditions for operating a hydrogenation in the second stage are generally familiar to those skilled in the art. The hydrogenation in the second hydrogenation stage may generally be performed at a pressure of 5 to 250 bar, preferably 10 to 150 bar, particularly preferably 15 to 30 bar. The pressure in the second hydrogenation stage could in principle be adjusted independently of the first hydrogenation stage. However, if the pressure in the second hydrogenation stage is to be higher this necessitates a certain apparatus complexity. It is therefore advantageous when the pressure in the second hydrogenation stage is lower than in the first hydrogenation stage. The temperature during hydrogenation in the second hydrogenation stage of the process according to the invention is preferably in the range from 100° C. to 220° C., preferably from 120° C. to 210° C., particularly preferably from 140° C. to 200° C.

The hydrogenation in the second hydrogenation stage may further be performed in the presence of a solvent inert or at least predominantly inert under the hydrogenation conditions. Inert solvents are known to those skilled in the art but are preferably selected from the group consisting of hydrocarbons and alcohols, preferably the alcohols obtained from the employed aldehydes. Alcohols can be converted into ethers over the support materials to a very small extent. However, in the context of the present invention this is nevertheless to be understood as meaning inert. The hydrogenation may also be performed in the presence of an aqueous phase, for example process water from the production of the aldehydes, entrained from the first hydrogenation stage, or from the hydrogenation itself. For the second hydrogenation stage it may also be preferable when an aqueous phase is additionally added to the hydrogenation. In the context of the present invention it is thus particularly preferable when no aqueous phase is added in the first hydrogenation stage but an aqueous phase, for example process water from the preceding production of the aldehydes or the hydrogenation itself, is added in the second hydrogenation stage.

The hydrogen-containing gas employed for the hydrogenation in the second hydrogenation stage may be either hydrogen or else a gas mixture which contains not only hydrogen but also one or more gases inert under hydrogenation conditions. It should be ensured that the amount of hydrogen is high enough to allow the hydrogenation to be performed to a sufficient extent. It is further preferable when the hydrogen is employed in a certain stoichiometric excess having regard to the aldehydes to be hydrogenated. The stoichiometric excess of hydrogen relative to the aldehydes to be hydrogenated is preferably in the range from 5% to 90%, particularly preferably between 20% and 70%, also in the second hydrogenation stage. The hydrogenation is thus preferably performed with a stoichiometric excess of hydrogen based on the aldehydes to be hydrogenated in both hydrogenation stages.

The reaction product obtained from the second hydrogenation stage which contains at least the alcohols formed and unconverted aldehydes may be worked up in familiar fashion, for example by separation of the excess/unconverted hydrogen and/or product separation by distillation, membrane separation or other suitable processes.

The present invention will now be elucidated with reference to examples. It will be appreciated that the examples show specific embodiments which are however not intended to limit the subject matter of the present invention.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European application No. 22158737.1, filed Feb. 25, 2022, are incorporated by reference herein.

Example 1 (Inventive)

The hydrogenation was carried out in two hydrogenation stages, wherein the first hydrogenation stage employed an activated metal catalyst based on a nickel metal foam (catalyst 1) and the second hydrogenation stage employed a supported catalyst comprising nickel and copper as the catalytically active component and aluminum oxide as the support material (catalyst 2). The supported catalyst is obtainable as Specialyst© 103 from Evonik Operations GmbH. The hydrogenation was performed with isononanal as the aldehyde.

Production of the activated metal catalyst based on a nickel metal foam (catalyst 1)

A nickel foam commercially available in rolls having a thickness of 1.9 mm, a width of 300 mm and an average pore size of 580 µm was sprayed with a commercially available polyethyleneimine adhesion promoter solution and coated with an aluminum powder (oxygen content: 0.5% by weight) containing 96.5% by weight of aluminum particles having a particle size<150 μm ($d_{90}$=68 μm) and subjected to a multistage heat treatment in the absence of oxygen at a temperature of not more than 725° C. The mass ratios of the employed nickel foam and aluminum powder were chosen such that the ratio of aluminum to the total mass of the supported alloy was 28±2%. Cooling was followed by a comminution of the material with a laser into cuboidal particles having an edge length of 4×4×1.9 mm. The resulting bulk material was activated by a 60 minute treatment in a 10% by weight aqueous sodium hydroxide solution at 60° C. The catalyst was then washed with DM water until achievement of a pH<10.

Molybdenum Doping 250 g of the freshly produced catalyst were treated with a 55.4% by weight ammonium heptamolybdate solution at room temperature over several hours until the molybdenum present in the solution had been completely deposited on the activated nickel foam catalyst. Monitoring of the molybdenum deposition was effected by detection of molybdenum in the supernatant solution with Merckoquant or Quantofix test strips. Treatment was terminated when molybdenum was no longer detectable in the supernatant solution. The catalyst was subsequently washed twice with DM water. The final catalyst contained more than 87% by weight of nickel, about 12% by weight of aluminum and less than 1% by weight of molybdenum.

Performing the Reaction

The hydrogenation of isononanal was carried out in a tubular reactor in recycle operation with a connected second tubular reactor in straight pass. The recycle tubular reactor had an internal diameter of 20.5 mm and a length of 730 mm. The second reactor had an internal diameter of 20.5 mm and a length of 1000 mm. The tubular reactors were operated with the liquid phase (isononanol and recycled hydrogenation product) and the gas phase (hydrogen) running in cocurrent in trickle bed mode. The recyclereactor employed 100 mL of catalyst 1 as hydrogenation catalyst. The second reactor employed 100 mL of catalyst 2. The feed rate of isononanol employed in the hydrogenation was 600 g/h. The recycle stream was 25 L/h. Hydrogen regulation (1.6 L/min-4 ml/min) was effected via a constant offgas mode with an offgas stream of 1 L/min. The experiments were each performed at a plant pressure of 26 bar in the recycle tubular reactor and 22.5 bar in the second tubular reactor. The reaction temperature in the recycle tubular reactor was varied between 130° C. and 170° C. A temperature of 180° C. was employed in the second tubular reactor. The output from the hydrogenation unit was analyzed by gas chromatography for the conversion of isononanal. The conversion of the isononanal after the second reactor was >99%. The experimental conditions are reported in table 2.

TABLE 2

| Overview of hydrogenation conditions | |
|---|---|
| Temperature of recycle reactor/° C. | 130-170 |
| Pressure of recycle reactor/bar | 26 |
| Feed rate of isononanal/gh$^{-1}$ | 600 |
| Recycle rate of liquid phase/Lh$^{-1}$ | 25 |
| Volume of catalyst in recycle reactor/mL (catalyst 1) | 100 |
| Length of catalyst bed/mm | 320 |
| Offgas/NLmin$^{-1}$ | 1 |
| WHSV/g of isononanal*(ml of catalyst * h)$^{-1}$ | 6 |

Example 2 (Noninventive)

Example 2 was performed in very much the same way as example 1. However, example 2 differs from example 1 in that the first hydrogenation stage and the second hydrogenation stage each employed a supported catalyst with nickel and copper as the catalytically active component and aluminum oxide as the support material (catalyst 2). In addition, 200 ml of catalyst 2 had to be employed in the recycle reactor and the feed rate of the isononanal had to be reduced to 230 g/h. A higher temperature of a constant 180° C. was also employed in the recycle reactor. The conversion of the isononanal after the second reactor was likewise>99%. An overview of the hydrogenation conditions may be found in table 3 which follows.

TABLE 3

| Overview of hydrogenation conditions | |
|---|---|
| Temperature of recycle reactor/° C. | 180 |
| Pressure of recycle reactor/bar | 26 |
| Feed rate of isononanal/gh$^{-1}$ | 230 |
| Recycle rate of liquid phase/Lh$^{-1}$ | 25 |
| Volume of catalyst in recycle reactor/mL (catalyst 1) | 200 |
| Length of catalyst bed/mm | 640 |
| Offgas/NLmin$^{-1}$ | 1 |
| WHSV/g of isononanal (ml of catalyst * h)$^{-1}$ | 1.15 |

It is very clear that the use of an activated metal catalyst based on a nickel metal foam in the first hydrogenation stage makes it possible to establish significantly higher feed rates and smaller catalyst volumes at unchanged conversions of >99%. The activated metal catalyst based on a nickel metal foam also makes it possible to use lower temperatures in the recycle reactor.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for producing alcohols by continuous hydrogenation of C9 aldehydes in at least two hydrogenation stages, wherein
a stream containing the C9 aldehydes to be hydrogenated is hydrogenated with a hydrogen-containing gas over an activated metal catalyst based on a nickel metal foam in the liquid phase in the first hydrogenation stage comprising at least one recycle reactor, wherein a crude product stream containing at least alcohols and unconverted aldehydes, of which a first portion is recycled and a second portion is passed to the second hydrogenation stage, is withdrawn from the at least one recycle reactor,
the second portion of the crude product stream is hydrogenated with a hydrogen-containing gas over a supported catalyst comprising a catalytically active component and a support material in the liquid phase in the second hydrogenation stage comprising at least one reactor operated in straight pass, wherein the catalytically active component is selected from the group consisting of nickel, copper, chromium and mixtures thereof and wherein the support material consists to an extent of more than 90% by weight of an oxidic material selected from the group consisting of aluminum oxide, aluminum silicate, silicon dioxide, titanium dioxide, zirconium oxide and mixtures of two or more thereof.

2. The process according to claim 1, wherein the stream employed in the process is an isononanal stream.

3. The process according to claim 1, wherein the activated metal catalyst based on a nickel metal foam is free from organic constituents, wherein free from organic constituents is defined as where the sum of the weight fractions of carbon and carbon-containing compounds is less than 0.2% by weight of the total weight of the catalyst.

4. The process according to claim 1, wherein the activated metal catalyst based on a nickel metal foam contains 80% to 95% by weight of nickel and 5% to 15% by weight of aluminum in each case based on the total weight of the catalyst.

5. The process according to claim 4, wherein the activated metal catalyst based on a nickel metal foam additionally contains 0.01% to 3% by weight of molybdenum, based on the total weight of the catalyst.

6. The process according to claim 1, wherein the hydrogenation in the first hydrogenation stage is performed at a pressure of 5 to 150 bar.

7. The process according to claim 1, wherein the hydrogenation in the first hydrogenation stage is performed at a temperature of 50° C. to 250° C.

8. The process according to claim 1, wherein the conversion of the hydrogenation in the first hydrogenation stage is at least 85%.

9. The process according to claim 1, wherein the volume fraction of the activated metal catalyst based on a nickel metal foam in the total catalyst volume of all hydrogenation stages is from 30% to 80%.

10. The process according to claim 1, wherein the support material of the supported catalyst is aluminum oxide, aluminum silicate or silicon dioxide.

11. The process according to claim 10, wherein the support material has a BET surface area of 70 to 350 m$^2$/g.

12. The process according to claim 1, wherein the hydrogenation in the second hydrogenation stage is performed at a pressure of 5 to 250 bar.

13. The process according to claim 1, wherein the hydrogenation in the second hydrogenation stage is performed at a temperature of 100° C. to 220° C.

14. The process according to claim 1, wherein the hydrogenation is carried out with a stoichiometric excess of hydrogen based on the aldehydes to be hydrogenated in both hydrogenation stages.

15. The process according to claim 1, wherein no aqueous phase is added in the first hydrogenation stage but an aqueous phase is added in the second hydrogenation stage.

* * * * *